(12) United States Patent  
Greer

(10) Patent No.: US 7,878,071 B2
(45) Date of Patent: Feb. 1, 2011

(54) NANOINDENTER TIP FOR UNIAXIAL TENSION AND COMPRESSION TESTING

(75) Inventor: Julia R. Greer, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 612 days.

(21) Appl. No.: 11/964,450

(22) Filed: Dec. 26, 2007

(65) Prior Publication Data

US 2010/0281963 A1     Nov. 11, 2010

Related U.S. Application Data

(60) Provisional application No. 60/876,899, filed on Dec. 22, 2006.

(51) Int. Cl.
*G01N 3/00* (2006.01)
*G01B 7/16* (2006.01)

(52) U.S. Cl. .......................... 73/794; 73/777

(58) Field of Classification Search ............ 73/760–860
See application file for complete search history.

(56) References Cited

U.S. PATENT DOCUMENTS

| | | | |
|---|---|---|---|
| 7,444,880 B2 * | 11/2008 | Zhang et al. | 73/779 |
| 7,681,459 B1 * | 3/2010 | Yang et al. | 73/856 |
| 7,752,916 B2 * | 7/2010 | Han et al. | 73/789 |
| 2004/0144180 A1 * | 7/2004 | Imamura | 73/796 |
| 2009/0164161 A1 * | 6/2009 | Hong et al. | 702/75 |
| 2010/0122572 A1 * | 5/2010 | Scherzinger et al. | 73/81 |

\* cited by examiner

*Primary Examiner*—Max Noori
(74) *Attorney, Agent, or Firm*—Milstein Zhang & Wu LLC; Joseph B. Milstein

(57) ABSTRACT

The invention is an indenter tip that is modified to permit both compression testing and tensile testing on samples having dimensions smaller than approximately 1 μm. The modified indenter tip has both a surface that can be used to apply compressive forces, and tines that can be used to engage a free end of a specimen to be tested in tension. The apparatus used to perform the tests includes elements of a scanning electron microscope that permit visualization of the specimen to be tested and the modified indenter tip, so as to permit appropriate alignment and engagement of the same. The apparatus also includes elements of a microindenter that provide mechanical manipulation of the relative position and orientation of the modified indenter tip and of the specimen to be tested, as well as the necessary controls and instrumentation to perform the test and to collect, record and manipulate data.

16 Claims, 8 Drawing Sheets

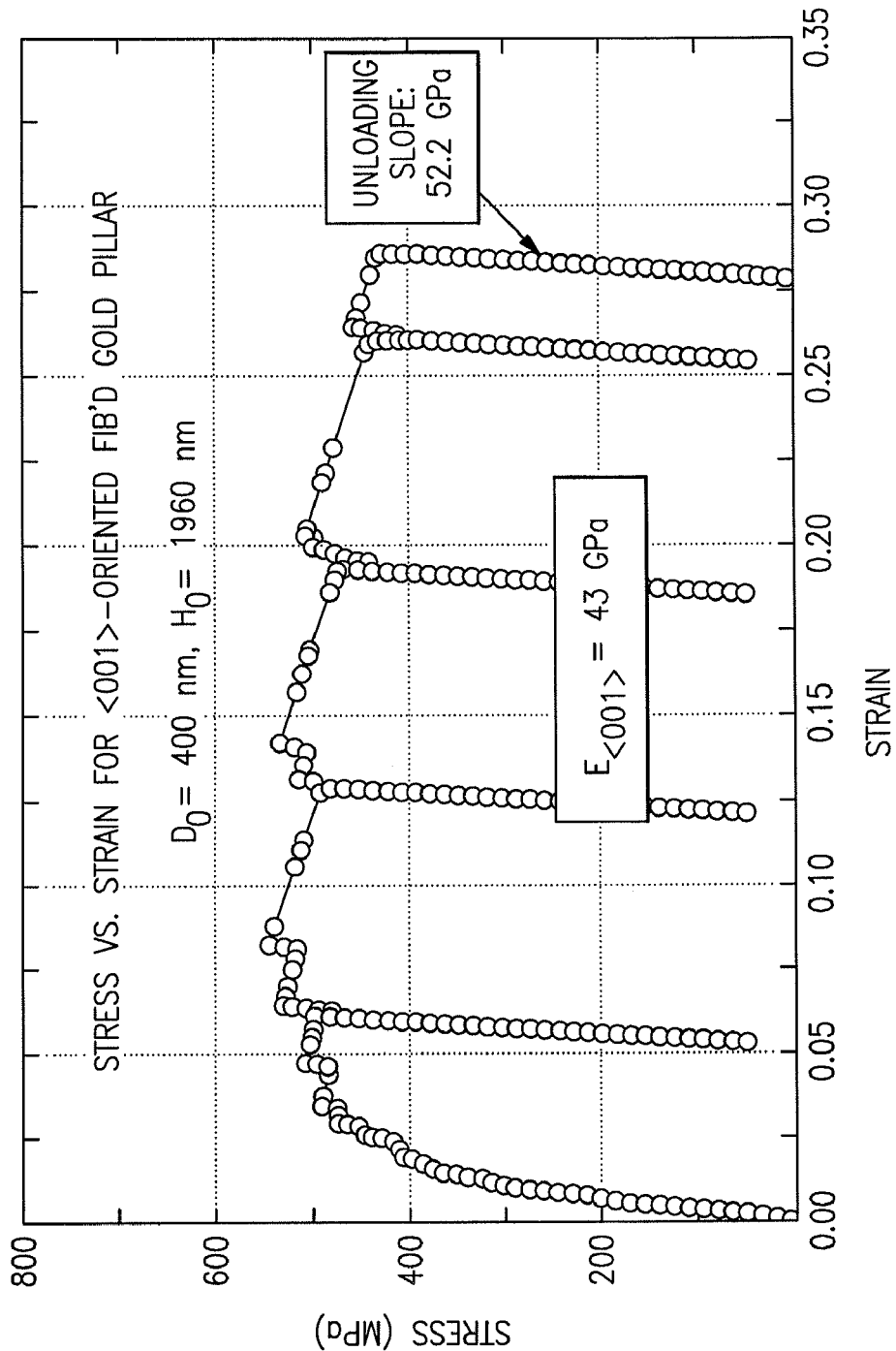

NANOINDENTER TIP FOR UNIAXIAL TENSION AND COMPRESSION TESTING

CROSS-REFERENCE TO RELATED APPLICATIONS

This application claims priority to and the benefit of U.S. provisional patent application Ser. No. 60/876,899, filed Dec. 22, 2006 which application is incorporated herein by reference in its entirety.

FIELD OF THE INVENTION

The invention relates to apparatus and methods for measuring mechanical properties of materials at the nano-scale, including crystalline and amorphous materials including polymers, biomaterials, metallic glasses, and single crystals in general and particularly to apparatus and methods that can perform measurements on nano-scale samples in both tension and compression.

BACKGROUND OF THE INVENTION

Mechanical testing of materials, including tensile and compression testing, is a well known art. In conventional mechanical testing, a macroscopic sample of a material of interest is prepared and is subjected to mechanical loads under various conditions to determine one or more parameters of interest. Various standards for performing mechanical testing have been described, including for example, ASTM International (formerly American Society for Testing and Materials or ASTM) standards. Conventional macroscopic crystalline samples generally comprise a plurality of sections having one or more of different crystallographic orientations, and different grain structures. Accordingly, a typical macroscopic specimen yields data that includes the effects of grain boundaries, thermal and mechanical treatments that can result in defects such as point defects, edge and screw dislocations, slip, stacking faults, and other defects.

In a tensile test, also known as a tension test, an axial pull is exerted upon the specimen of interest in accordance with agreed upon standards, and the results measured with scientifically accurate methods. Examples of parameters and relationships that can be determined using tensile testing include true stress and strain, engineering stress and strain, the elastic modulus, the ultimate tensile strength, the fracture stress, the modulus of toughness, and the modulus of resilience.

A compression test determines behavior of materials under loads that may be sufficient even to crush the specimen of interest. The specimen is compressed and deformation at various loads is recorded. Commonly, compressive stress and strain are calculated and plotted as a stress-strain diagram which is used to determine elastic limit, proportional limit, yield point, yield strength and, for some materials, compressive strength.

The ASM Handbook®, Vol. 8, *Mechanical Testing and Evaluation*, ASM International, Materials Park, Ohio 44073-0002, states: "Axial compression testing is a useful procedure for measuring the plastic flow behavior and ductile fracture limits of a material. Measuring the plastic flow behavior requires frictionless (homogenous compression) test conditions, while measuring ductile fracture limits takes advantage of the barrel formation and controlled stress and strain conditions at the equator of the barreled surface when compression is carried out with friction. Axial compression testing is also useful for measurement of elastic and compressive fracture properties of brittle materials or low-ductility materials. In any case, the use of specimens having large L/D ratios should be avoided to prevent buckling and shearing modes of deformation."

Hardness testing is conventionally performed using an indenter that is pressed into a surface of a material, and the resulting deformation is examined and quantified. Examples of standard hardness measurements include Rockwell hardness, Vickers hardness, and Brinell hardness.

Up to now, the application of such testing procedures to nano-scale specimens has not been convenient, and to the inventor's knowledge, no one has performed tensile testing on such specimens. In the field of testing of nano-scale specimens of materials of interest, mechanical deformation has largely been carried out in thin films due to their relative ease of deposition and their industrial relevance. Thin films' mechanical properties like the elastic modulus, hardness, and stress-strain can be determined via nanoindentation, which involves indenting a sharp diamond tip into the material and measuring the load as a function of displacement into the surface. In all nanoindentation studies, a so-called size effect is observed, which manifests itself as an increase in hardness at shallower indentation depths. Various groups of scientists and engineers are studying size effects in small specimens by uniaxial compression of nano-pillars, nanotube and nanowire forests. In these experiments, a nanoindenter with a flat tip is used to conduct compression tests rather than nanoindentation tests. This testing capability proves to be useful in any nano-scale fabrication as it provides a reliable way of assessing the mechanical properties of a structure, such as elastic response, yield stress, and possibly fatigue parameters. Although a unified theory explaining plasticity below a certain length scale remains a matter of great research and controversy, the results of most computational and experimental studies indicate that smaller is always stronger. Therefore, it has been determined that mechanical properties of a particular material are different at the nano-scale and cannot be inferred from its bulk properties.

While these nano-compression experiments are effective for determination of some of the mechanical parameters at the nano-scale, they are mainly used by research groups and are not commercially available. Moreover, there is a need to have additional mechanical characterization techniques for nano-scale samples. For example, reliability concerns in MEMS and NEMS fabrication usually require the knowledge of a material's strength, ductility, tensile toughness, and fracture toughness, which most likely differ from those in the bulk. These and other properties can be obtained by performing tension rather than compression experiments. Tension experiments currently present a great experimental challenge and have not been widely performed. It is believed that there are only two in-situ SEM systems capable of compression load-displacement measurements, one at the Wright-Patterson Air Force Base and one at EMPA, an affiliate of the Swiss Federal Institute of Technology. Neither system is equipped with the tensile testing capability at the desired scale, below 1 µm.

There is a need for systems and methods for making tensile (and also compression) tests on nano-scale specimens, in order to determine the fundamental materials properties.

SUMMARY OF THE INVENTION

In one aspect, the invention relates to a manipulation apparatus configured to be operated in both tension and compression on specimens having dimensions below 1 µm. The manipulation apparatus comprises a tip having at least one surface in a first plane, the at least one surface configured to apply a compressive force to a first test specimen having a dimension below 1 μm, the first test specimen to be placed in compression when the first test specimen is attached to a support. The tip further has a pair of tines substantially oriented in an orientation parallel to the first plane. The pair of tines is configured to apply a tension force to a second test specimen having a dimension below 1 μm, the second test specimen to be placed in tension when the second test specimen is attached to a support. The pair of tines each have a root and a tip, a first of the pair of tines having a first surface oriented substantially perpendicular to the first plane, a second of the pair of tines having a second surface oriented substantially perpendicular to the first plane, the first surface of the first tine and the second surface of the second tine connected at the respective roots, the first surface of the first tine and the second surface of the second tine oriented at an angle relative to each other such that the first surface of the first tine and the second surface of the second tine are configured to form a "V"-shaped aperture that becomes wider as one traverses a respective one of the tines from the root to the tip, the "V"-shaped aperture configured to engage a substantially linear extent of the second test specimen to be placed in tension. The tines each have an additional surface opposite the at least one surface configured to apply the compressive force to the first test specimen, the additional surface configured to engage the second test specimen to be placed in tension at a wider portion of the second test specimen than the substantially linear extent of the second test specimen. The tip is configured to perform either or both of compression and tension tests on respective first and second test specimens to be tested in compression and tension successively.

In one embodiment, the manipulation apparatus further comprises a support for a selected one of the first test specimen and the second test specimen, and a manipulator stage configured to operate at nanometer resolution, the manipulator stage configured to allow a respective orientation and positioning of the test specimen and the tip so that the tip engages the test specimen in a manner suitable for the conduct of a test. In one embodiment, the manipulation apparatus further comprises a visualization system configured to display for a user the position and orientation of the test specimen and the position and orientation of the tip. In one embodiment, the visualization system comprises an electron beam manipulation portion, and a video display portion. In one embodiment, the manipulation apparatus further comprises a user interface configured to adjust the respective orientation and positioning of the test specimen and the tip in response to a command issued by the user. In one embodiment, the manipulation apparatus further comprises a control module having a user interface, the control module configured to perform a selected one of a compression test and a tension test on the test specimen in response to a command issued by the user, the control module configured to data-log and record a result of the selected test. In one embodiment, the control module is a general purpose programmable computer.

In another aspect, the invention features a process of testing a nano-scale specimen having dimensions below 1 μm. The process comprises the step of providing, in a chamber configured to allow a user to manipulate and to visualize specimens having dimensions below 1 μm, a testing tip. The testing tip has at least one surface in a first plane, the at least one surface is configured to apply a compressive force to a first test specimen having a dimension below 1 μm, the first test specimen to be placed in compression when the first test specimen is attached to a support. The testing tip has a pair of tines substantially oriented in an orientation parallel to the first plane, the pair of tines configured to apply a tension force to a second test specimen having a dimension below 1 μm, the second test specimen to be placed in tension when the second test specimen is attached to a support; the pair of tines each having a root and a tip, a first of the pair of tines having a first surface oriented substantially perpendicular to the first plane, a second of the pair of tines having a second surface oriented substantially perpendicular to the first plane, the first surface of the first tine and the second surface of the second tine connected at the respective roots, the first surface of the first tine and the second surface of the second tine oriented at an angle relative to each other such that the first surface of the first tine and the second surface of the second tine are configured to form a "V"-shaped aperture that becomes wider as one traverses a respective one of the tines from the root to the tip, the "V"-shaped aperture configured to engage a substantially linear extent of the second test specimen to be placed in tension, the tines each having an additional surface opposite the at least one surface configured to apply the compressive force to the first test specimen, the additional surface configured to engage the second test specimen to be placed in tension at a wider portion of the second test specimen than the substantially linear extent of the second test specimen. Additional steps in the process include providing a specimen having dimensions below 1 μm; selecting a tension test measurement to be performed on the specimen; positioning the testing tip and the specimen relative to each other so that the testing tip and the specimen are engaged for the selected measurement; performing the selected measurement; and recording at least one parameter of the selected test and at least one result of the selected test of the specimen, the at least one recorded parameter and at least one recorded result being available for later analysis so as to determine a property or a behavior of the test specimen.

In one embodiment, the chamber configured to allow a user to manipulate and to visualize specimens having dimensions below 1 μm comprises a chamber having an electron beam manipulation portion therein. In one embodiment, the chamber configured to allow a user to manipulate and to visualize specimens having dimensions below 1 μm comprises a chamber having therein a manipulator configured to manipulate the tip and the specimen under control by a control module or by a user. In one embodiment, the control module is a general purpose programmable computer. In one embodiment, the step of positioning the testing tip and the specimen relative to each other so that the testing tip and the specimen are engaged for the selected measurement comprises at least one step of the following four steps: contacting a free end of the specimen to be tested in tension with the indenter; moving the indenter so as to be mechanically clear of the specimen to be tested; moving the specimen to be tested and the indenter relative to each other so that the indenter tip is positioned so as to engage the specimen using the "V"-shaped aperture; and orienting the modified indenter tip so that the "V"-shaped aperture is oriented appropriately to engage the specimen to be tested in tension, and positioning the modified indenter tip and the specimen so that the desired engagement of the "V"-shaped aperture about a relatively linear segment of the specimen to be tested is accomplished. In one embodiment, the selected measurement is a tension measurement.

In one embodiment, the process of testing a nano-scale specimen having dimensions below 1 μm further comprises the step of a user watching the measurement in real-time. In one embodiment, the process of testing a nano-scale specimen having dimensions below 1 μm further comprises the step of playing back in slow motion the recorded parameter or the recorded result so as to make events of the measurement visible to a human observer. In one embodiment, the process of testing a nano-scale specimen having dimensions below 1

μm further comprises the step of performing a compression test measurement on a second test specimen.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

FIG. 3 is a diagram showing a typical stress-strain curve for <001> gold nanopillars in compression, characterized by many discrete segments.

DETAILED DESCRIPTION OF THE INVENTION

The present invention relates to a nanoindenter tip modification that enables effective methods for testing mechanical properties of materials at the nano-scale both in tension and in compression, for example using components of the MTS Nanoindenter. The procedure for measuring specific mechanical properties is described. To enhance our knowledge of mechanical response at nano-scale, new testing methods need to be developed where the results can be directly compared with simulations aimed at the development of plasticity laws based on dislocation structure.

Figure 1:
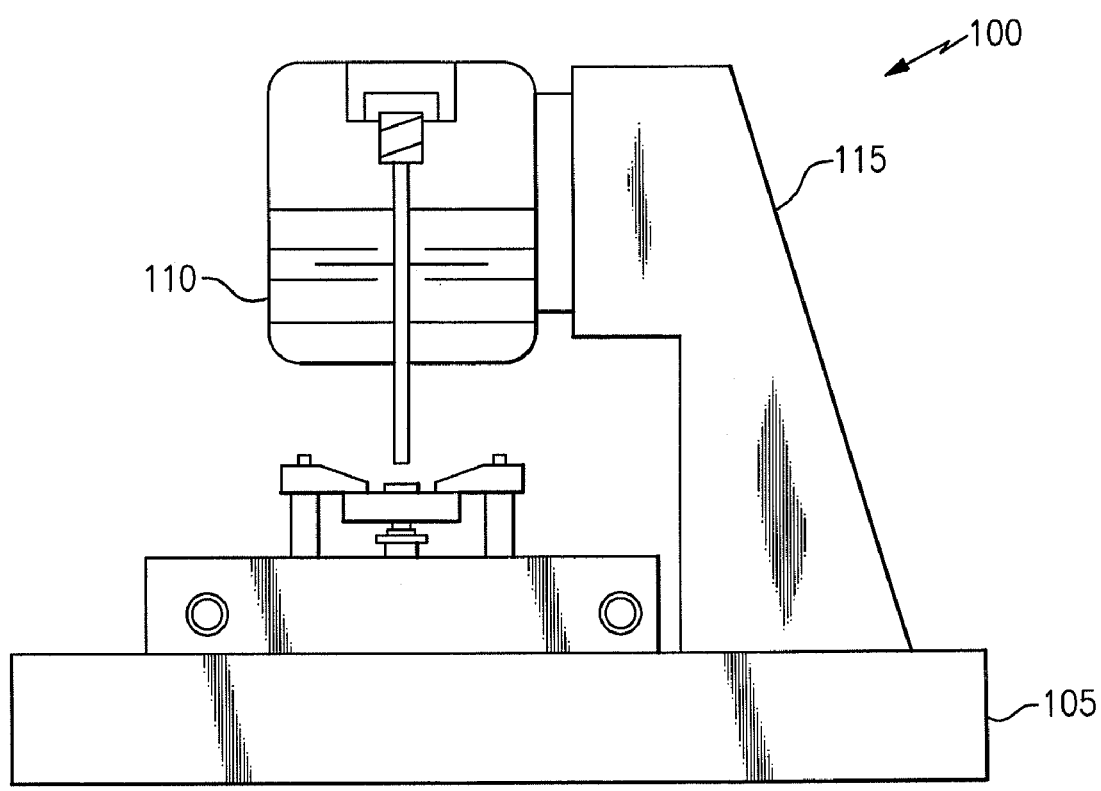
FIG. 1 is a schematic diagram of an MTS nanoindenter, including the features needed to perform a typical nanoindentation experiment, according to the prior art.

The basic principle of the nanoindenter operation involves pressing an indenter tip into a material of interest. The nanoindenter imposes a load on the sample by sending a current through a load coil, and then measures displacement using a three-plate capacitor. A schematic of a MTS Nanoindenter, available from MTS Nano Instruments, 701 Scarboro Road, Suite 100, Oak Ridge, Tenn. 37830, with its basic functional components is shown in FIG. 1. This instrument has the load resolution on the order of 50 nN and a displacement resolution on the order of 0.02 nm, which enables the users to probe very small volumes. The particular indenter shape allows for calculation of the cross-sectional deformation area as a function of displacement. Hardness, which is defined as the load divided by the contact area, can then be calculated as a measure of the deformation resistance of the material.

FIG. 1 is a schematic diagram 100 of an MTS nanoindenter, including the features needed to perform a typical nanoindentation experiment. In FIG. 1, there is shown a sample supported by an x-y translator stage connected to a base 105, and an indenter having a diamond tip connected to an actuator/sensor 110 supported by a vertical translator connected to a vertical support arm 115 connected to the base 105. The actuator/sensor 110 includes a magnet, a loading coil, typically two leaf springs and a displacement gage. In use, the diamond tipped indenter is positioned relative to the sample by moving the sample using the x-y translation stage to locate a region of the sample to be tested by indentation beneath the indenter tip, and by lowering the indenter and the actuator/sensor 110 using the vertical translator until the region to be tested is immediately below the indenter tip. The apparatus has the ability to sense when the indenter tip just comes into contact with the specimen of interest (e.g., to detect the surface of the specimen of interest) through the change in stiffness. The indenter tip is then pressed into the sample by operating the loading coil, and the depth of penetration is measured using the displacement gage. The properties of the sample can be deduced from the force applied to the indenter and the corresponding depth of penetration, using well known mathematical procedures that will not be described in detail here.

Commercial nanoindenters are generally equipped with a standard set of diamond indenter tips mainly for performing nanoindentation experiments. These tips generally have the shape of a sharp 3-faced pyramid (Berkovich and Cube Corner) or a sphere. The results of recent work have demonstrated the possibility of standard tip modification in order to perform uniaxial compression measurements in small samples. This modification involves flattening the sharp indenter tip by the use of a Focused Ion Beam (FIB). The nanoindenter 200 having a plane surface that results from the modification is shown in perspective in FIG. 2.

Figure 2:
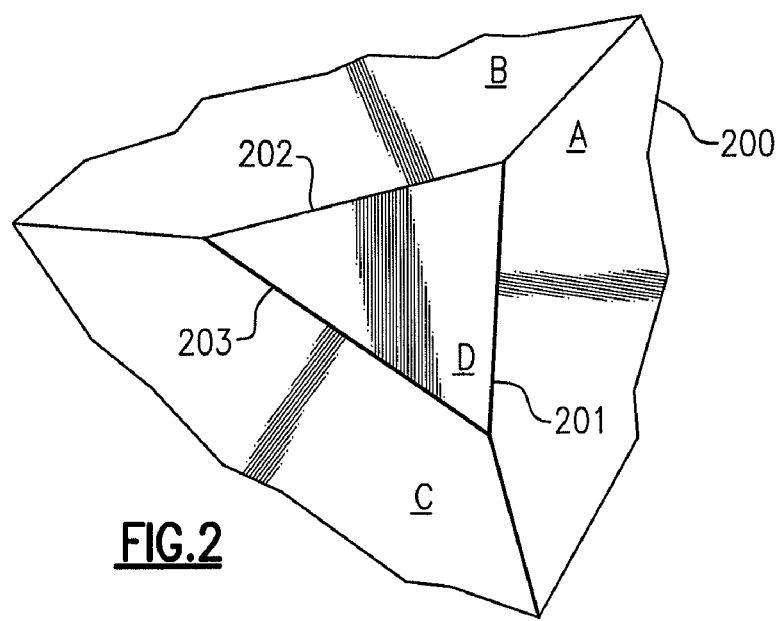
FIG. 2 is a diagram showing a perspective view of a Berkovich diamond indenter with a FIB-flattened tip.

In FIG. 2, there are three planar faces denoted A, B and C that are disposed in relative orientations to form the 3-faced pyramidal tip. By milling away material with the FIB, a flat facet denoted D is produced, having an edge 201 at the intersection of the plane of facet D with face A, an edge 202 at the intersection of the plane of facet D with face B, and an edge 203 at the intersection of the plane of facet D with face C. Facet D is configured to have a plane (hereinafter the first plane) perpendicular to an intended axial direction of motion of the nano-indenter. In FIG. 2, the approximate lengths of edges 201, 202 and 203 are 15 to 17 μm.

Figure 4A:
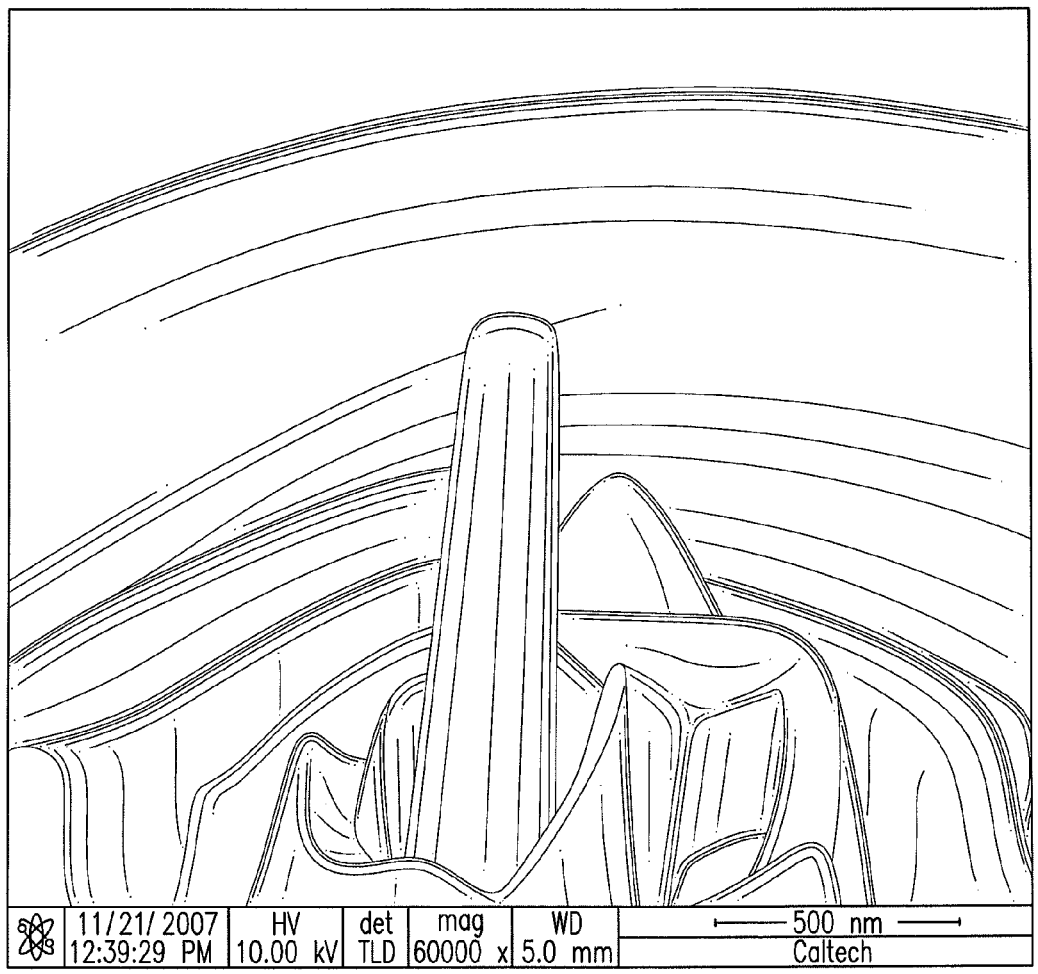
FIG. 4A and FIG. 4B show SEM images of single crystal <001> Molybdenum pillars before after compression, showing multiple slip lines that are produced by the compression.
Figure 4B:
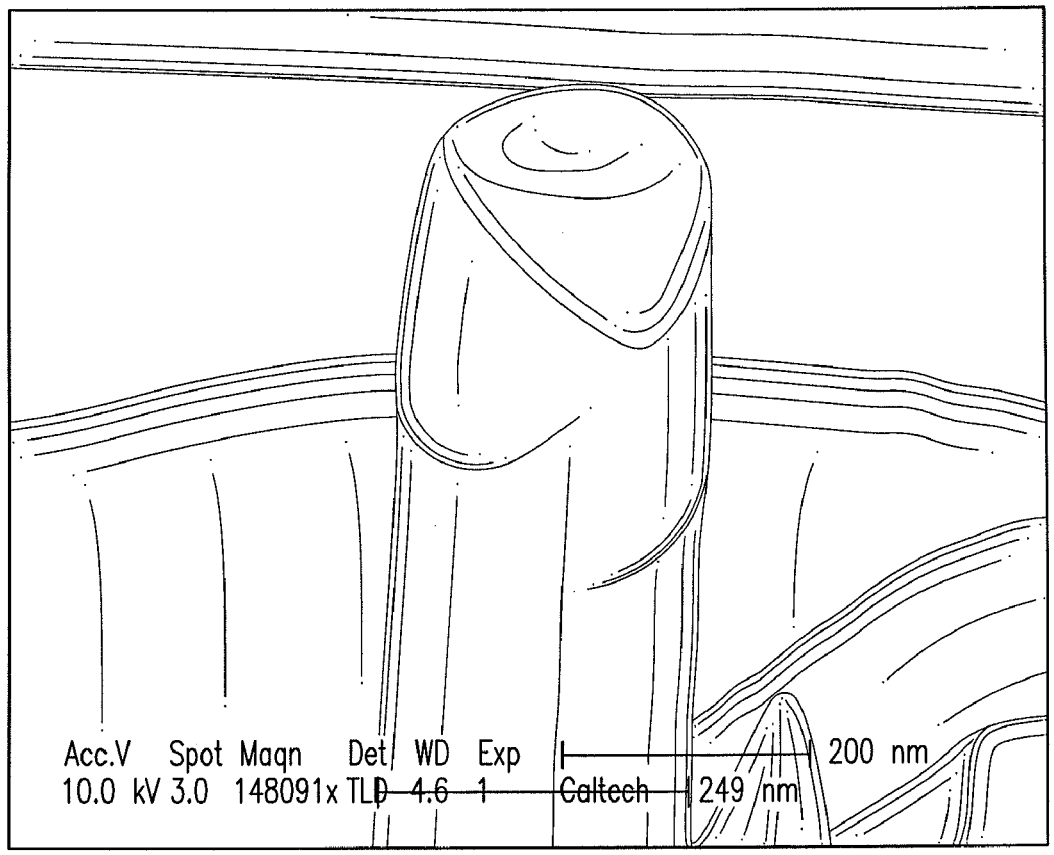
Figure 4C:
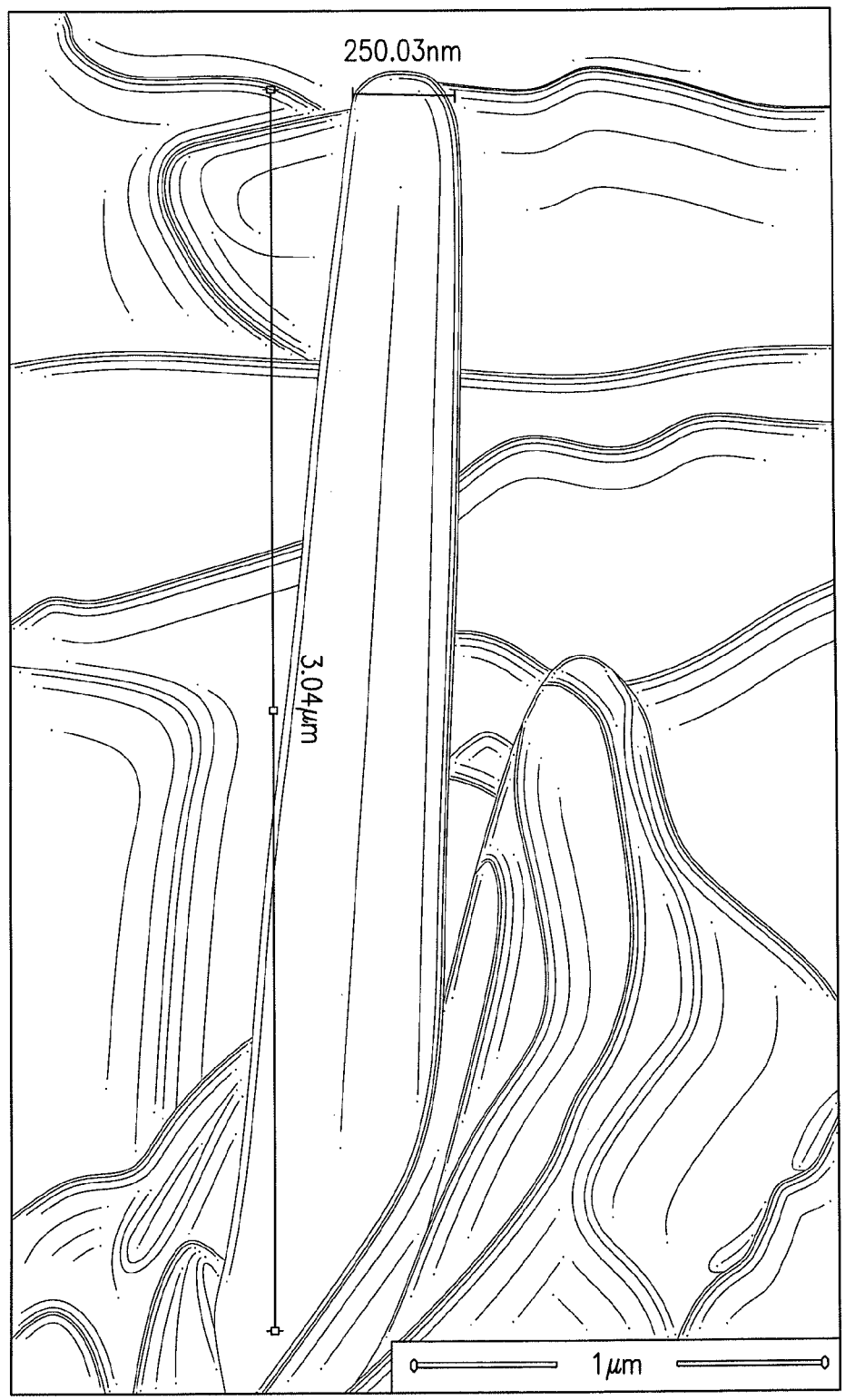
FIG. 4C and FIG. 4D show SEM images of single crystal <001> Gold pillars before after compression, showing multiple slip lines that are produced by the compression.
Figure 4D:
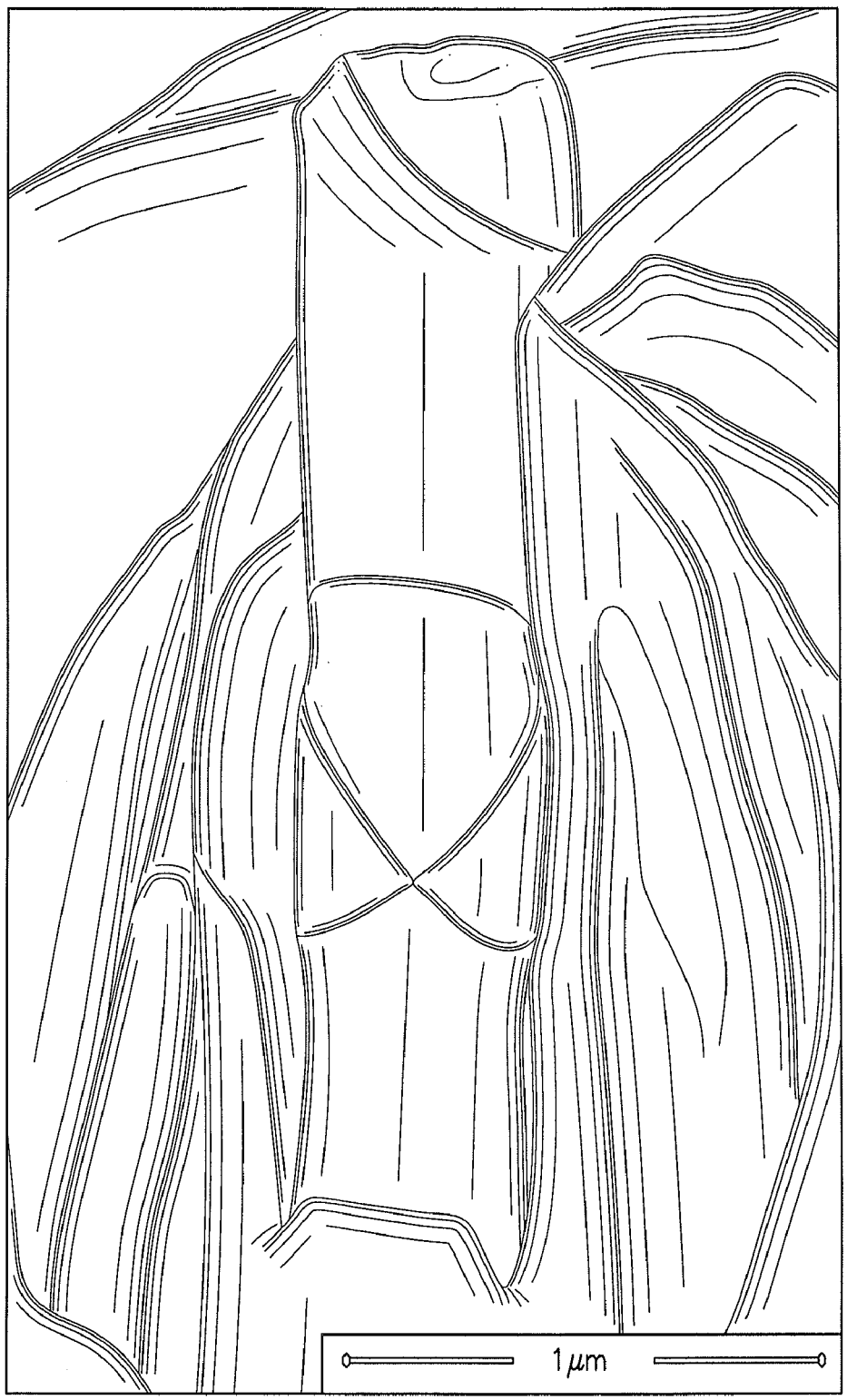

An example showing the results of a compression experiment using such a modified tip is shown in FIG. 3. FIG. 3 is a diagram showing a typical stress-strain curve for <001>-oriented gold nanopillars in compression, characterized by many discrete segments. SEM images corresponding to a gold pillar before and after compression are also presented in FIG. 3. This example involves a homogeneous deformation experiment accomplished by uniaxial compression of small pillars with a flattened indenter tip, in which one imposes a load at a prescribed loading or displacement rate while measuring the length change of the specimen. There is now some literature describing the compressive behavior of several different metals, including single crystals, polycrystalline, and nanoporous materials. This technique is beneficial in assessing the stress and stiffness of the material as a function of strain in compression. It is, however, limited in its ability to observe any dynamic effects in the sense that the tests are performed "blindly," with only the "before and after" states available for reviewing. It also is constrained to only one type of deformation. A characteristic compressive stress-strain curve for a gold nano-pillar usually has many discrete so-called strain bursts, which happen on the order of nano-seconds, as shown in FIG. 3. FIG. 4A and FIG. 4B show SEM images of single crystal <001> Molybdenum pillars before after compression, showing multiple slip lines that are produced by the compression. FIG. 4C and FIG. 4D show SEM images of single crystal <001> Gold pillars before after compression, showing multiple slip lines that are produced by the compression. These events are extremely challenging to capture or to interrupt, as the instrument's ability to remove the load in response to such a fast event is limited.

The invention further involves an improvement of a standard indenter tip through specific modifications that allow the user not only to perform uniaxial compression tests but also to measure the tensile response of a material of interest. It is also expected that torsional tests may also be possible using the modified nanoindenter tip of the invention. Since the properties of materials have been found to vary with the sample size once the nano-scale regime is reached, this invention provides a powerful technique for determination of such parameters as nano-scale fracture toughness, ultimate tensile strength (UTS), yield criteria in tension, tensile toughness, and possibly the torsional response of a material of interest. The ultimate tensile strength is obtained along with the yield strength and the strain at fracture during tensile experiments. Materials having both high UTS and high fracture strains are called "tough," which is a desirable property for most mechanical designs, especially in MEMS and NEMS.

The specific tip configuration for tensile testing involves fabrication of triangular tensile grips from a standard cube corner or Berkovich indenter tip, as shown in FIG. 5 through FIG. 8. This can be accomplished by utilizing the Focused Ion Beam (FIB) or another nano-scale precision machining technique to create at least two tines that define a "V"-shaped aperture (or a wedge-shaped opening) that can be used to engage and grip a specimen for tensile testing, while leaving enough of the surface defined by the first plane to permit compression testing of specimens as well. Separate samples are used for a compression test and a tensile test, e.g., performing both tests involves at least two specimens. Samples can be prepared in situ, or can be prepared separately and introduced into the testing apparatus.

Figure 5:
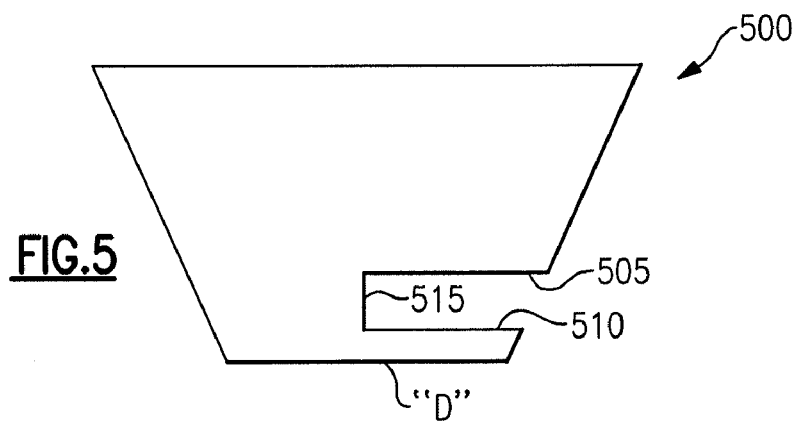
FIG. 5 is a diagram showing the tension-modified indenter tip in side view, according to principles of the invention.

FIG. 5 is a diagram 500 showing the tension-modified indenter tip in side view. In FIG. 5 the facet D of the modified nanoindenter is shown at the bottom. A portion of the material of the nanoindenter is removed to provide a channel defined by the surfaces 505, 510 and 515 as seen in the side view. Surfaces 505 and 515 are preferably parallel to surface D, that is, parallel to the first plane previously defined hereinabove.

Figure 6:
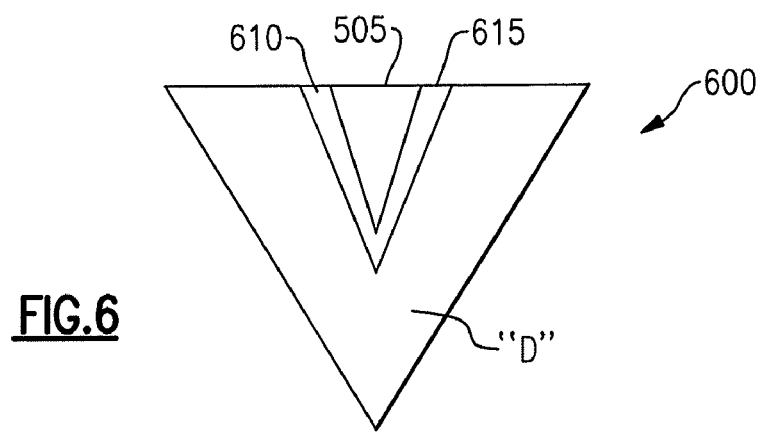
FIG. 6 is a diagram showing the tension-modified indenter tip in bottom view, according to principles of the invention.

FIG. 6 is a diagram 600 showing the tension-modified indenter tip in bottom view. As can be seen in FIG. 6, a section of the bottom surface D remains unmodified, to provide a surface useful for compression testing. In the bottom view of FIG. 6, two tines having surfaces 610 and 615 are also shown. The two tines are configured to apply a tension force to a test specimen having a dimension below 1 µm. The test specimen can be placed in tension when the test specimen is attached to a support, such as that in the apparatus shown in FIG. 1. The exposed portion of surface 505 as seen from the bottom view in FIG. 6 is also useful for compression testing of a sample that can come in contact with surface 505.

Each tine of the pair of tines has a root and a tip. The tines extend from the root to the tip, in a direction that is preferably parallel to the first plane. The tines have surfaces 610 and 615 that are oriented substantially perpendicular to the first plane. The surfaces 610 and 615 are connected at the respective roots of the tines; the surfaces 610 and 615 are oriented at an angle relative to each other such that they configured to form a "V"-shaped aperture that becomes wider as one traverses a respective one of the tines from the root to the tip. The "V"-shaped aperture is configured to engage a substantially linear extent of a test specimen to be placed in tension.

Figure 7:
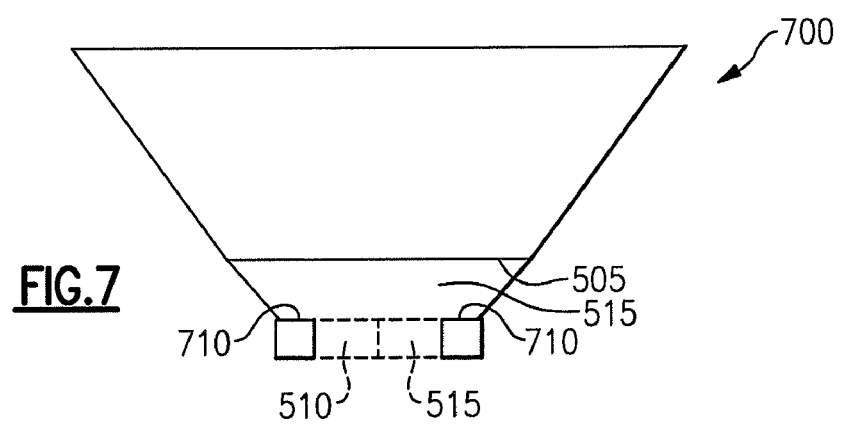
FIG. 7 is a diagram showing the tension-modified indenter tip in front view, according to principles of the invention.

FIG. 7 is a diagram 700 showing the tension-modified indenter tip in front view. In FIG. 7, the tines are observed to each have an additional surface 710 (that portion of surface 510 that remains after the tines are defined by removal of material) opposite the surface D. The additional surfaces 710 are configured to engage a test specimen to be placed in tension at a wider portion of the second test specimen than the substantially linear extent of the second test specimen. For example, a test specimen that is shaped like a nail having a nail head can be engaged along its linear extent by the surfaces 610, 615 of the tines, and the nail head portion can fit within the aperture defined by the surfaces 505, 510, 515 so that the test specimen can be placed in tension when the nano-indenter shown in FIG. 5 through FIG. 8 is moved so as to pull on the test specimen because surfaces 610 will engage the nail head portion.

Figure 8:
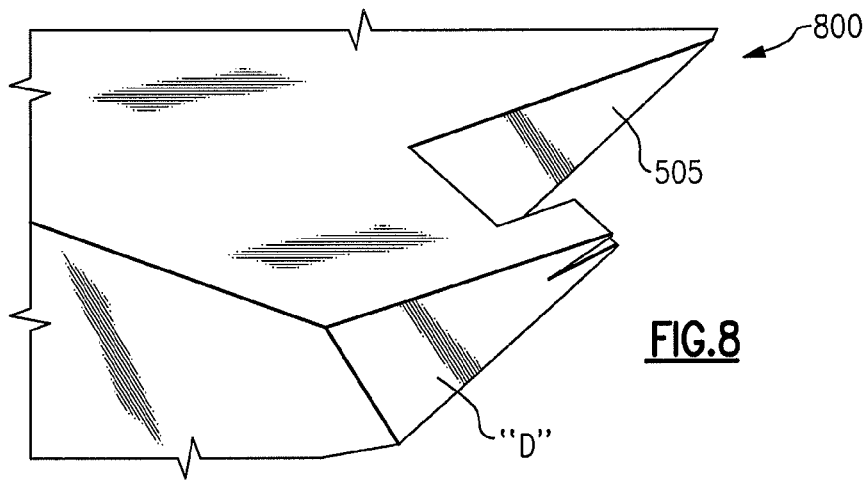
FIG. 8 is a diagram showing the tension-modified indenter tip in perspective view, according to principles of the invention.

FIG. 8 is a diagram showing the tension-modified indenter tip in perspective view, including both the first plane and the remaining portion of surface D, the tines, and a portion of surface 515 parallel to surface D.

An important advantage of the triangular geometry of the wedge-shaped opening is its universal ability to support a wide variety of sample diameters by clamping them into the "wedge" on the indenter bottom. Another advantage of this indenter tip is its ability to perform both compression and tension tests since the flat base (e.g., surface D) that can be used for uniaxial compression is a part of this design. Having described the modifications of the nano-indenter tip, we now turn to a discussion of the operation of the apparatus, and the process of making compression and tension measurements.

Once the tension-compression tip modification is performed, the indenter tip can be inserted into the instrument via a standard operating procedure. All applicable calibration and operation procedures associated with the use of the instrument remain the same and will not be affected by the insertion of the new tip. Specifically, surface detection, load-displacement data collection, and continuous stiffness measurement during deformation can be performed as usual.

Unlike compression tests, tension experiments will allow for determination of ultimate tensile strength (UTS), or the highest stress reached before fracture, and tensile toughness, or a material's ability to absorb energy without fracture. Brittle materials generally have low tensile toughness, despite their high strengths, due to their low ductility. The availability of a tensile testing technique at the nano-scale can reveal a different behavior where high-strength materials would also have high tensile toughness, resulting in desirable structural integrity.

The new tensile testing is performed on a free-standing specimen attached to a rigid substrate. The instrument is operated in the continuous stiffness measurement, or CSM mode. The principle of the CSM technique involves the application of a small displacement oscillation, resulting in a corresponding load oscillation. The load amplitude and the displacement amplitude are related to the contact stiffness, which is determined continuously. Hence, the indenter can sense the change in the stiffness once it comes in contact with the sample. Once the specimen is detected, the indenter tip is preferably raised by ~5 µm, and the sample stage is moved a specified small distance laterally to position the sample behind the tensile grips using the x-y translator. The indenter can then be lowered slightly to its contact position, and the specimen can be moved laterally so that the indenter can engage and hold the specimen. This procedure is illustrated in FIG. 9 through FIG. 12. Once the sample is gripped, the indenter can be used in a standard fashion as if during an "unloading" segment of nanoindentation or compression experiments.

Turning now to the procedure by which the indenter can engage a specimen to be tested in tension, it is noteworthy that the process is performed in an apparatus that includes the necessary components of a scanning electron microscope that make possible real-time visualization of the positions of the modified indenter tip and of the specimen to be tested, so that a user can manipulate those relative positions to have the modified indenter tip engage the specimen to be tested in tension. The following steps are performed at least under the observation and control of a user, whether or not explicitly under the direct control of the user using suitable input devices such as a pointing device, a joystick, a keyboard, or another input device, and a visualization display such as a video display, or under the control of a general purpose programmable computer functioning as a controller.

Figure 9:
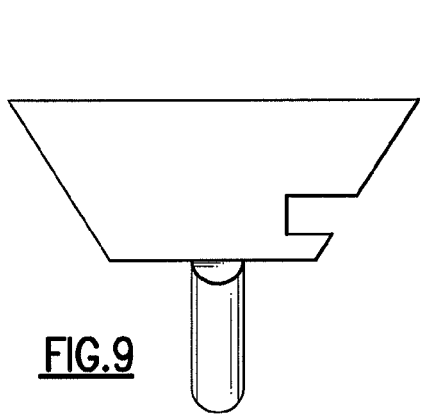
FIG. 9 is a diagram schematically illustrating an indenter in contact with a sample to be tested in tension, according to principles of the invention.

FIG. 9 is a diagram schematically illustrating an indenter in contact with a sample to be tested in tension. As a first step of the process of testing a specimen in tension, the indenter is brought into contact with the free end of the specimen to be tested in tension so as to determine or identify the position of the free end of the specimen. This step is some embodiments may be optional if there is some other convenient way to determine the location of the free end of the specimen to be tested in tension.

Figure 10:
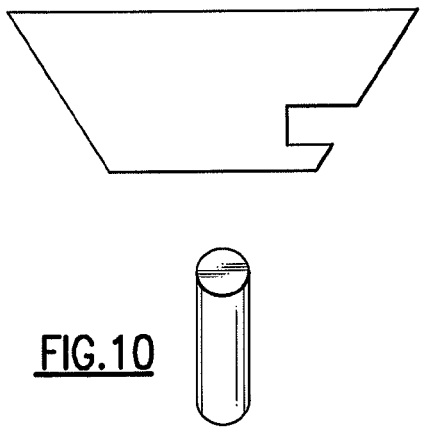
FIG. 10 is a diagram schematically illustrating an indenter after it moves up slightly above the sample, according to principles of the invention.

FIG. 10 is a diagram schematically illustrating an indenter after it moves up slightly above the sample. In another step of the process of testing the specimen in tension, the indenter is moved so as to be mechanically clear of the specimen to be tested.

Figure 11:
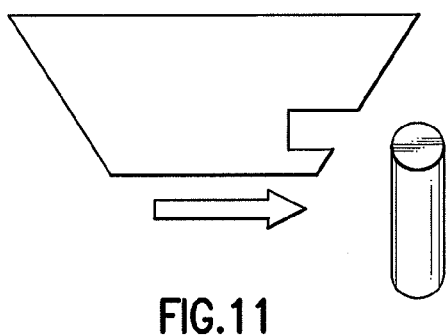
FIG. 11 is a diagram schematically illustrating an indenter comes down to position itself, according to principles of the invention.

FIG. 11 is a diagram schematically illustrating an indenter comes down to position itself. In a further step, the specimen to be tested and the indenter are moved relative to each other so that the indenter tip can be positioned so as to engage the specimen using the "V"-shaped aperture. The relative motions can be accomplished by moving either or both of the indenter tip and the specimen. As an example, starting with the relative positioning shown in FIG. 10, the specimen is moved using the x-y translator stage to be clear of the indenter, and the indenter is then moved closer to the support holding the specimen so that the "V"-shaped aperture is aligned with the specimen, and is ready to engage the specimen.

Figure 12:
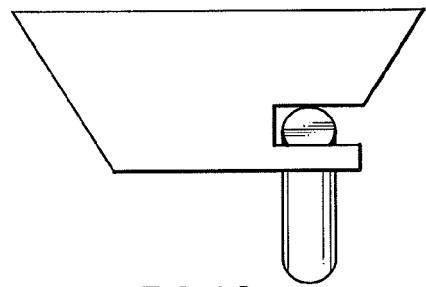
FIG. 12 is a diagram schematically illustrating how the indenter grips the specimen for a tension test, according to principles of the invention.

FIG. 12 is a diagram schematically illustrating how the indenter grips the specimen for a tension test. In another step, the modified indenter tip is oriented so that the "V"-shaped aperture is oriented appropriately to engage the specimen to be tested in tension, and the modified indenter tip and the specimen are positioned so that the desired engagement of the "V"-shaped aperture about a relatively linear segment of the specimen to be tested is accomplished. In FIG. 9 through FIG. 12, the "nail-head" portion of the specimen to be tested is omitted, but should be understood to be present, so that the two tines of the modified indenter tip can apply a tensional force to the specimen to be tested in tension. In some instances, the modified indenter tip is expected to be able to hold a specimen that lacks a "nail head" portion.

Once the modified indenter tip and the specimen to be tested in tension are engaged, the user can initiate a tension test that is performed by the apparatus under the control of a general purpose programmable computer operating with suitable instructions provided in the form of at least one program recorded on a machine-readable medium. In the apparatus of the invention, the test is performed with the use of the SEM visualization capability, so that a user can, if he or she so desires, watch the test in real-time. The test parameters and data as well as the visualization signals can all be recorded for later analysis and/or review, as may be desired. In some instances, the events that occur during a test happen in so short a period that they are "invisible" to a human observer in real-time, but can be made visible to a human observer by playing back the recorded data or the recorded visualization signals in slow motion, so that the events that occur in a shorter time appear to be taking place in a longer time interval, and become visible to a human observer. In the extreme, the playback can involve stepping through one or more individual recorded images, so that each such image is displayed for a time, for example a period of time controlled by a viewer of the image or images. The playback can involve stepping through images in a sequence of images recorded earlier followed by images recorded later, or in a sequence of images recorded later followed by images recorded earlier.

Tension-Compression Asymmetry

Manufacturing devices with sub-micron critical feature sizes requires a thorough understanding of how the materials from which those features are constructed will respond to mechanical deformation. At sub-micron dimensions, not only do factors like material, size, and geometry appear to play a role in determining mechanical behavior, but crystallographic orientation and type of deformation also appear to be key parameters. There are reports that address the differences in material strength when subjected to tension vs. compression. For example, Diao et al performed Embedded Atom Method (EAM) molecular dynamics simulations and showed that the yield strength asymmetry in gold nanowires for two different orientations (<001> and <111>) is attributed to the surface-induced internal stress. Tomar et al observed this asymmetry in nanocrystalline $\alpha$-$Fe_2O_3$-fcc Al composites and attributed it to the differences in grain boundary sliding mechanisms. Lund et al demonstrated that nanocrystalline Ni has higher yield and flow stresses in compression rather than in tension for both uniaxial and biaxial simulations, and they likened the operating atomistic-level mechanism to the shear transformation zones (STZs) operating in metallic glasses. There are also several pressure-dependent analytical models that predict tension/compression asymmetry in nanocrystalline materials. Most of these studies focused on plastic deformation due to the heterogeneities at nano-scale (grain boundaries, etc.); however the influence of free surfaces and crystallographic orientation on dislocation behavior in the absence of these heterogeneities (single crystal) also has to be investigated to provide a more complete understanding of plasticity. The inventor believes that there has been no literature description with experimental results for single crystals or nano-crystalline materials, which meaningfully compared the findings with simulation results since the grains are generally larger than the Hall-Petch breakdown size. The tensile capability provided by the present invention permits one to conduct such tension experiments at the appropriate scale and to be able to relate the findings to the computational results described above.

Instrumentation: Design of In-Situ SEM/Nanoindenter (SEMentor)

It is also expected that the present invention will enable the development of a new instrument, with in-situ tension and compression capabilities, which will offer the advantage of measuring mechanical response while capturing the dynamic effects. For these mechanical testing experiments, it is expected that the strengths of two instruments, the Scanning or Secondary Electron Microscope (SEM) and the Nanoindenter can be combined to produce a novel instrument, referred to as the "SEMentor". The SEMentor comprises a FEG Quanta-200 SEM, available from FET Company 5350 NE Dawson Creek Drive, Hillsboro, Oreg. 97124, and the DCM unit of the Nanoindenter assembly placed in one of the ports so that one can do in-situ testing. It is expected that the instrument can additionally comprise a FIB (Focused Ion Beam) in addition to the Nanoindenter. In such an instrument, it is expected that one can make the specimen in the same instrument, as well, which cannot be done in a SEM.

The instrument is expected to offer a precise control and high resolution of load and displacement (and their rates) and contact stiffness during the experiment while the former allows for visualization of the process (albeit not at the atomic scale).

To achieve atomic resolution, there are some groups working on micro-compression and nanoindentation in the in-situ TEM. Integration of SEM (rather than TEM) into mechanical testing can be extremely powerful because (1) it allows for testing a wide range of length scales, from several nanometers to several hundred microns, (2) it does not restrict the samples to be crystalline, and (3) sample preparation is not difficult. We expect that the instrument will be useful to perform uniaxial experiments, i.e. compression and tension.

In-situ compression and tension is expected to allow one to correlate the macroscopic stress-strain behavior with some discrete dislocation activity by direct observation of the dislocation glide "avalanches," which are manifested by multiple slip lines, as shown in FIG. 4. It will also enable one to validate the homogeneity of the deformation and only choose those samples that deform uniformly, reducing the experimental data scatter currently present in the literature. The SEM will offer the advantage of taking frame-by-frame images during the deformation, enabling one to create movies of the deformation capturing some of the dynamic effects. It will also provide the much-needed visualization capability and stage motion precision, which will not only validate the homogeneity of the deformation during compression but will also allow to perform tension experiments, which are currently impossible to perform in a conventional Nanoindenter chamber. Tensile deformation will be extremely useful, for example, in determining the origins of tension/compression asymmetry observed in nano-crystalline materials as well as in single crystals.

General Purpose Programmable Computers

General purpose programmable computers useful for controlling instrumentation, recording signals and analyzing signals or data according to the present description can be any of a personal computer (PC), a microprocessor based computer, a portable computer, or other type of processing device. The general purpose programmable computer typically comprises a central processing unit, a storage or memory unit that can record and read information and programs using machine-readable storage media, a communication terminal such as a wired communication device or a wireless communication device, an output device such as a display terminal, and an input device such as a keyboard. The display terminal can be a touch screen display, in which case it can function as both a display device and an input device. Different and/or additional input devices can be present such as a pointing device, such as a mouse or a joystick, and different or additional output devices can be present such as an enunciator, for example a speaker, a second display, or a printer. The computer can run any one of a variety of operating systems, such as for example, any one of several versions of Windows, or of MacOS, or of Unix, or of Linux.

In operation, a general purpose programmable computer is programmed with instructions in the form of software or firmware. The instructions control the operation of the general purpose programmable computer/The general purpose programmable computer can perform a variety of manipulations of data, such as mathematical operations (e.g., calculations), logical operations (e.g., comparisons, or logical deductions following defined rules), and processing of textual or graphical data (e.g., word processing, or image processing). Data can be provided to the general purpose programmable computer as recorded data or as real-time data. The result of any computation or processing operation is recorded in a machine-readable medium or memory for immediate use or for future use. For example, in micro-processor based analysis modules, data can be recorded in a register in a microprocessor, in a cache memory in the microprocessor, in local memory such as semiconductor memory (e.g., SRAM, DRAM, ROM, EPROM), magnetic memory (e.g., floppy disc or hard disc) and/or optical memory (e.g., CD-ROM, DVD, HD-DVD), or in a remote memory such as a central database. Future use of data recorded in a machine-readable medium can include displaying, printing, or otherwise communicating the data to a user, using the data in a further calculation or manipulation, or communicating the data to another computer or computer-based device.

Machine-readable storage media that can be used in the invention include electronic, magnetic and/or optical storage media, such as magnetic floppy disks and hard disks; a DVD drive, a CD drive that in some embodiments can employ DVD disks, any of CD-ROM disks (i.e., read-only optical storage disks), CD-R disks (i.e., write-once, read-many optical storage disks), and CD-RW disks (i.e., rewriteable optical storage disks); and electronic storage media, such as RAM, ROM, EPROM, Compact Flash cards, PCMCIA cards, or alternatively SD or SDIO memory; and the electronic components (e.g., floppy disk drive, DVD drive, CD/CD-R/CD-RW drive, or Compact Flash/PCMCIA/SD adapter) that accommodate and read from and/or write to the storage media. As is known to those of skill in the machine-readable storage media arts, new media and formats for data storage are continually being devised, and any convenient, commercially available storage medium and corresponding read/write device that may become available in the future is likely to be appropriate for use, especially if it provides any of a greater storage capacity, a higher access speed, a smaller size, and a lower cost per bit of stored information. Well known older machine-readable media are also available for use under certain conditions, such as punched paper tape or cards, magnetic recording on tape or wire, optical or magnetic reading of printed characters (e.g., OCR and magnetically encoded symbols) and machine-readable symbols such as one and two dimensional bar codes.

Theoretical Discussion

Although the theoretical description given herein is thought to be correct, the operation of the devices described and claimed herein does not depend upon the accuracy or validity of the theoretical description. That is, later theoretical developments that may explain the observed results on a basis different from the theory presented herein will not detract from the inventions described herein.

While the present invention has been particularly shown and described with reference to the structure and methods disclosed herein and as illustrated in the drawings, it is not confined to the details set forth and this invention is intended to cover any modifications and changes as may come within the scope and spirit of the following claims.

What is claimed is:

1. A manipulation apparatus configured to be operated in both tension and compression on nano-scale specimens having dimensions below 1 μm, comprising:
   a tip having at least one surface in a first plane, said at least one surface configured to apply a compressive force to a first test specimen having a dimension below 1 μm, said first test specimen to be placed in compression when said first test specimen is attached to a support; and
   said tip further having a pair of tines substantially oriented in an orientation parallel to said first plane, said pair of tines configured to apply a tension force to a second test specimen having a dimension below 1 μm, said second test specimen to be placed in tension when said second test specimen is attached to a support;
   said pair of tines each having a root and a tip, a first of said pair of tines having a first surface oriented substantially perpendicular to said first plane, a second of said pair of tines having a second surface oriented substantially perpendicular to said first plane, said first surface of said first tine and said second surface of said second tine connected at said respective roots, said first surface of said first tine and said second surface of said second tine oriented at an angle relative to each other such that said first surface of said first tine and said second surface of said second tine are configured to form a "V"-shaped aperture that becomes wider as one traverses a respective one of said tines from said root to said tip, said "V"-shaped aperture configured to engage a substantially linear extent of said second test specimen to be placed in tension, said tines each having an additional surface opposite said at least one surface configured to apply said compressive force to said first test specimen, said additional surface configured to engage said second test specimen to be placed in tension at a wider portion of said second test specimen than said substantially linear extent of said second test specimen;
   said tip being configured to perform either or both of compression and tension tests on respective first and second test specimens to be tested in compression and tension successively.

2. The manipulation apparatus configured to be operated in both tension and compression on nano-scale specimens having dimensions below 1 μm of claim 1, further comprising a support for a selected one of said first test specimen and said second test specimen, and a manipulator stage configured to operate with nanometer precision, said manipulator stage configured to allow a respective orientation and positioning of said test specimen and said tip so that said tip engages said test specimen in a manner suitable for the conduct of a test.

3. The manipulation apparatus configured to be operated in both tension and compression on nano-scale specimens having dimensions below 1 μm of claim 2, further comprising a visualization system configured to display for a user said position and orientation of said test specimen and said position and orientation of said tip.

4. The manipulation apparatus configured to be operated in both tension and compression on nano-scale specimens having dimensions below 1 μm of claim 3, wherein said visualization system comprises an electron beam manipulation portion, and a video display portion.

5. The manipulation apparatus configured to be operated in both tension and compression on nano-scale specimens having dimensions below 1 μm of claim 2, further comprising a user interface configured to adjust said respective orientation and positioning of said test specimen and said tip in response to a command issued by said user.

6. The manipulation apparatus configured to be operated in both tension and compression on nano-scale specimens having dimensions below 1 μm of claim 2, further comprising a control module having a user interface, said control module configured to perform a selected one of a compression test and a tension test on said test specimen in response to a command issued by said user, said control module configured to data-log and record a result of said selected test.

7. The manipulation apparatus configured to be operated in both tension and compression on nano-scale specimens having dimensions below 1 μm of claim 6, wherein said control module is a general purpose programmable computer.

8. A process of testing a nano-scale specimen having dimensions below 1 μm, comprising the steps of:
   providing, in a chamber configured to allow a user to manipulate and to visualize specimens having dimensions below 1 μm, a testing tip having:
      at least one surface in a first plane, said at least one surface configured to apply a compressive force to a first test specimen having a dimension below 1 μm, said first test specimen to be placed in compression when said first test specimen is attached to a support; and
      having a pair of tines substantially oriented in an orientation parallel to said first plane, said pair of tines configured to apply a tension force to a second test specimen having a dimension below 1 μm, said second test specimen to be placed in tension when said second test specimen is attached to a support;
      said pair of tines each having a root and a tip, a first of said pair of tines having a first surface oriented substantially perpendicular to said first plane, a second of said pair of tines having a second surface oriented substantially perpendicular to said first plane, said first surface of said first tine and said second surface of said second tine connected at said respective roots, said first surface of said first tine and said second surface of said second tine oriented at an angle relative to each other such that said first surface of said first tine and said second surface of said second tine are configured to form a "V"-shaped aperture that becomes wider as one traverses a respective one of said tines from said root to said tip, said "V"-shaped aperture configured to engage a substantially linear extent of said second test specimen to be placed in tension, said tines each having an additional surface opposite said at least one surface configured to apply said compressive force to said first test specimen, said additional surface configured to engage said second test specimen to be placed in tension at a wider portion of said second test specimen than said substantially linear extent of said second test specimen;
   providing a specimen having dimensions below 1 μm;
   selecting a tension test measurement to be performed on said specimen;
   positioning said testing tip and said specimen relative to each other so that said testing tip and said specimen are engaged for said selected measurement;
   performing said selected measurement; and
   recording at least one parameter of said selected test and at least one result of said selected test of said specimen, said at least one recorded parameter and at least one recorded result being available for later analysis so as to determine a property or a behavior of said test specimen.

9. The process of testing a nano-scale specimen having dimensions below 1 μm of claim 8, wherein said chamber configured to allow a user to manipulate and to visualize specimens having dimensions below 1 μm comprises a chamber having an electron beam manipulation portion therein.

10. The process of testing a nano-scale specimen having dimensions below 1 μm of claim 8, wherein said chamber configured to allow a user to manipulate and to visualize specimens having dimensions below 1 μm comprises a chamber having therein a manipulator configured to manipulate said tip and said specimen under control by a control module or by a user.

11. The process of testing a nano-scale specimen having dimensions below 1 μm of claim 10, wherein said control module is a general purpose programmable computer.

12. The process of testing a nano-scale specimen having dimensions below 1 μm of claim 8, wherein said step of positioning said testing tip and said specimen relative to each other so that said testing tip and said specimen are engaged for said selected measurement comprises at least one step of the following four steps:
   contacting a free end of said specimen to be tested in tension with said indenter;
   moving said indenter so as to be mechanically clear of said specimen to be tested;
   moving said specimen to be tested and said indenter relative to each other so that said indenter tip is positioned so as to engage said specimen using said "V"-shaped aperture; and
   orienting said modified indenter tip so that said "V"-shaped aperture is oriented appropriately to engage said specimen to be tested in tension, and positioning said modified indenter tip and said specimen so that said desired engagement of said "V"-shaped aperture about a relatively linear segment of said specimen to be tested is accomplished.

13. The process of testing a nano-scale specimen having dimensions below 1 μm of claim 8, wherein said selected measurement is a tension measurement.

14. The process of testing a nano-scale specimen having dimensions below 1 μm of claim 8, further comprising the step of a user watching said measurement in real-time.

15. The process of testing a nano-scale specimen having dimensions below 1 μm of claim 8, further comprising the step of playing back in slow motion said recorded parameter or said recorded result so as to make events of said measurement visible to a human observer.

16. The process of testing a nano-scale specimen having dimensions below 1 μm of claim 8, further comprising the step of performing a compression test measurement on a second test specimen.

* * * * *